(12) United States Patent
Davies et al.

(10) Patent No.: US 11,179,042 B2
(45) Date of Patent: Nov. 23, 2021

(54) APPARATUS AND METHOD OF CHARACTERISING A NARROWING IN A FLUID FILLED TUBE

(75) Inventors: Helen Catherine Stuart Davies, London (GB); Justin Davies, London (GB)

(73) Assignee: MEDSOLVE LIMITED, London (GB)

( * ) Notice: Subject to any disclaimer, the term of this patent is extended or adjusted under 35 U.S.C. 154(b) by 1407 days.

(21) Appl. No.: 13/978,697

(22) PCT Filed: Jan. 6, 2012

(86) PCT No.: PCT/GB2012/050015
§ 371 (c)(1),
(2), (4) Date: Sep. 13, 2013

(87) PCT Pub. No.: WO2012/093260
PCT Pub. Date: Jul. 12, 2012

(65) Prior Publication Data
US 2013/0345574 A1    Dec. 26, 2013

(30) Foreign Application Priority Data

Jan. 6, 2011 (GB) .................................. 1100136

(51) Int. Cl.
*A61B 5/02* (2006.01)
*A61B 5/0215* (2006.01)
(Continued)

(52) U.S. Cl.
CPC ........ *A61B 5/02007* (2013.01); *A61B 5/0215* (2013.01); *A61B 5/02158* (2013.01);
(Continued)

(58) Field of Classification Search
CPC .......... A61M 2025/0002; A61M 25/09; A61B 5/0215; A61B 5/02158; A61B 5/6851
See application file for complete search history.

(56) References Cited

U.S. PATENT DOCUMENTS

| 4,691,709 A | 9/1987 | Cohen et al. |
| 6,354,999 B1 * | 3/2002 | Dgany .................. A61B 1/015 600/486 |

(Continued)

FOREIGN PATENT DOCUMENTS

| CN | 1758873 | 4/2006 |
| CN | 1921904 A | 2/2007 |

(Continued)

OTHER PUBLICATIONS

Chinese State Intellectual Property Office, "Notification of Second Office Action" for Application No. 201280004868.8, dated Sep. 7, 2015, 11 pages with translation.
International Searching Authority/European Patent Office, "International Search Report and The Written Opinion of the International Searching Authority," for PCT/GB2012/050015, dated Apr. 20, 2012, 14 pages.

(Continued)

*Primary Examiner* — Christian Jang
*Assistant Examiner* — Karen E Toth (57) ABSTRACT

A system and method for characterising a narrowing in a fluid filled tube, the system comprising: a probe having a first measurement sensor to take an instantaneous measurement at different locations along the tube; a mechanism to draw the probe through the tube; a position measure to provide location data relating to the location at which a respective instantaneous measurement is taken by the first measurement sensor; a processor to calculate, from the instantaneous measurements, a characteristic of the tube at different locations along the tube.

34 Claims, 7 Drawing Sheets

(51) Int. Cl.
  *A61B 5/103* (2006.01)
  *A61B 5/00* (2006.01)
  *A61M 25/09* (2006.01)
  *A61M 25/00* (2006.01)

(52) U.S. Cl.
  CPC ............ *A61B 5/103* (2013.01); *A61B 5/6851* (2013.01); *A61M 25/09* (2013.01); *A61M 2025/0002* (2013.01)

(56) References Cited

U.S. PATENT DOCUMENTS

| | | | |
|---|---|---|---|
| 6,473,635 | B1 | 10/2002 | Rasche |
| 7,693,563 | B2 | 4/2010 | Suresh et al. |
| 2002/0072880 | A1 | 6/2002 | Svanerudh et al. |
| 2003/0216621 | A1 | 11/2003 | Alpert et al. |
| 2004/0176683 | A1* | 9/2004 | Whitin ............... A61B 5/068 600/424 |
| 2005/0187461 | A1* | 8/2005 | Murphy .............. G09B 23/28 600/416 |
| 2007/0055090 | A1 | 3/2007 | Neustadter et al. |
| 2007/0100239 | A1 | 5/2007 | Nair et al. |
| 2010/0234698 | A1* | 9/2010 | Manstrom ......... A61B 5/02028 600/301 |
| 2010/0298734 | A1* | 11/2010 | Colman .............. A61B 5/087 600/543 |
| 2012/0041735 | A1 | 2/2012 | Taylor |

FOREIGN PATENT DOCUMENTS

| | | | |
|---|---|---|---|
| JP | 2002513601 A | | 5/2002 |
| WO | WO 01/13779 A2 | * | 3/2001 |
| WO | WO 2001/013779 | * | 3/2001 ......... A61B 5/02007 |
| WO | WO2006041346 | | 4/2006 |
| WO | WO2011038044 | | 3/2011 |

OTHER PUBLICATIONS

Korean Office Action dated Aug. 21, 2014 in Korean Patent Application No. 2013-7020711, filed Jan. 6, 2012.
Chinese State Intellectual Property Office, "Notification of First Office Action" for Application No. 201280004868.8, dated Jan. 9, 2015, 14 pages with translation.
Canadian Intellectual Property Office, "Examination Report," for Application No. 2,823,805, dated Feb. 12, 2015, 5 pages.
New Zealand Intellectual Property, "First Examination Report," for Application No. 613148, dated Dec. 6, 2013, 3 pages.
Patent Application in New Zealand No. 613148, in connection with a Substantive Examination Report issued by the New Zealand Patent Office, dated Aug. 11, 2015, 5, pages.
Israeli Patent Office, Office Action for Application No. 227353, dated Aug. 9, 2016, 2 pages.
Chinese State Intellectual Property Office, "Notification of Fourth Office Action" for Application No. 201280004868.8, dated May 6, 2016, 20 pages with translation.
Israeli Office Action dated Mar. 2, 2017, Application No. 227353, 3 pages.
Notice of Opposition in EP Application No. 12825326.7, Feb. 23, 2018.
Communication of a Notice of Opposition in EP Application No. 12825326.7, Mar. 1, 2018.
Taylor, C.A., "Patient-Specific Modeling of Cardiovascular Mechanics", Annual Review of Biomedical Engineering, vol. 11, Apr. 13, 2009, pp. 109-127.
Sen et al., Development and Validation of a New Adenosine-Independent Index Stenosis Severity from Coronary Wave-Intensity Analysis, Journal of the American College of Cardiology, vol. 59, No. 15, 2012, pp. 1392-1402.
Chinese State Intellectual Property Office, "Notification of Third Office Action" for Application No. 201280004868.8, dated Nov. 25, 2015, 7 pages with translation.

* cited by examiner

Cumulative change in iPR

APPARATUS AND METHOD OF CHARACTERISING A NARROWING IN A FLUID FILLED TUBE

CROSS-REFERENCE TO RELATED APPLICATION

This application is a United States national phase application of international patent application number PCT/GB2012/050015, filed Jan. 6, 2012, which claims the benefit of GB Application No. 1100136.9 filed Jan. 6, 2011, the disclosure of which is incorporated herein by reference.

FIELD OF THE INVENTION

This invention relates to an apparatus and method of characterising a narrowing in a fluid filled tube.

BACKGROUND TO THE INVENTION

An example of a fluid filled tube or vessel formed with a constriction or narrowing is a blood vessel having a stenosis. Assessment or measurement of the constriction is helpful to review the extent and location of the constriction.

Figure 1:
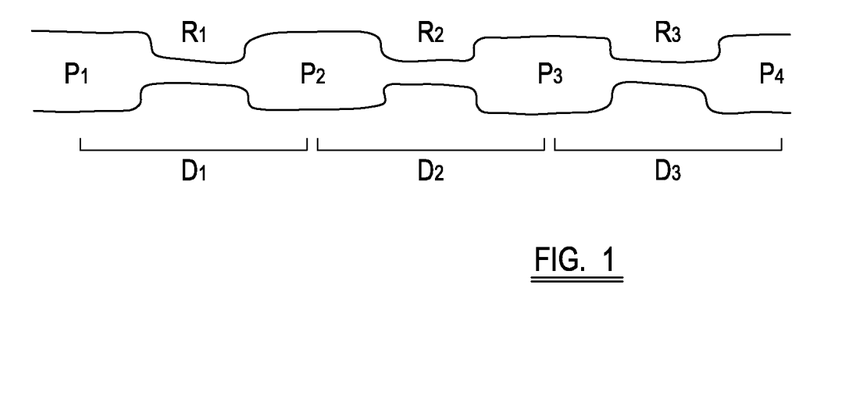
FIG. 1 is a schematic diagram of a series of constrictions in a fluid filled tube, where P is pressure, R is a ratio of the pressures and D is the distance between measurements.

A methodology for assessment of a constriction in a fluid filled tube such as a coronary stenosis is fractional flow reserve (FFR). This technique measures the drop in pressure at two points along a vessel; see FIG. 1 of the accompanying drawings where example points P1 and P4 identify where measurements of pressure and flow rate can be taken, under conditions of maximal achievable hyperemia in a coronary environment. The Pd measurement comes from a pressure sensor on the wire and the Pa measurement comes from the catheter. A comparison is then made by expressing the mean distal pressure (Pd), as a proportion of mean proximal pressure (Pa), wherein the values are mean Pa and Pd over the entire cardiac cycle, taken over at least one complete cardiac cycle (but usually an average of 3 or more beats):

$$\text{Fractional Flow Reserve}(FFR) = \frac{P_d}{P_a}$$

It is an object of the invention to provide an apparatus and method of profiling or characterising a narrowing in a fluid filled tube.

One aspect of the present invention provides system for characterising a narrowing in a fluid filled tube, the system comprising: a probe having a first measurement sensor to take an instantaneous measurement at different locations along the tube; a mechanism to draw the probe through the tube; a position measure to provide location data relating to the location at which a respective instantaneous measurement is taken by the first measurement sensor; a processor to calculate, from the instantaneous measurements, a characteristic of the tube at different locations along the tube.

Another aspect of the present invention provides a probe for assessing a characteristic of a fluid filled tube comprising two measurement sensors spaced apart by a known distance and a line between the two sensors, the line being drawable through the tube to alter the known distance between the first sensor and the second sensor.

A further aspect of the present invention provides a method of characterising a narrowing in a fluid filled tube using a probe having a sensor, comprising: drawing the probe within the tube along the tube; recording probe sensor readings at different locations along the tube; and calculating, from the instantaneous measurements, a characteristic of the tube at different locations along the tube.

A yet further aspect of the present invention provides a probe for assessing a characteristic of a fluid filled tube comprising two measurement sensors and a line between the two sensors, the line being drawable through the tube to alter the distance between the first sensor and the second sensor.

BRIEF DESCRIPTION OF THE DRAWINGS

In order that the present invention may be more readily understood, embodiments of the invention will now be described with reference to the accompanying drawings, in which.

DESCRIPTION

This invention provides an apparatus and method of profiling or characterising a narrowing in a fluid filled tube. The apparatus and method of profiling or characterising is also useful to characterise or profile a series of narrowings in a fluid filled tube.

Figure 2:
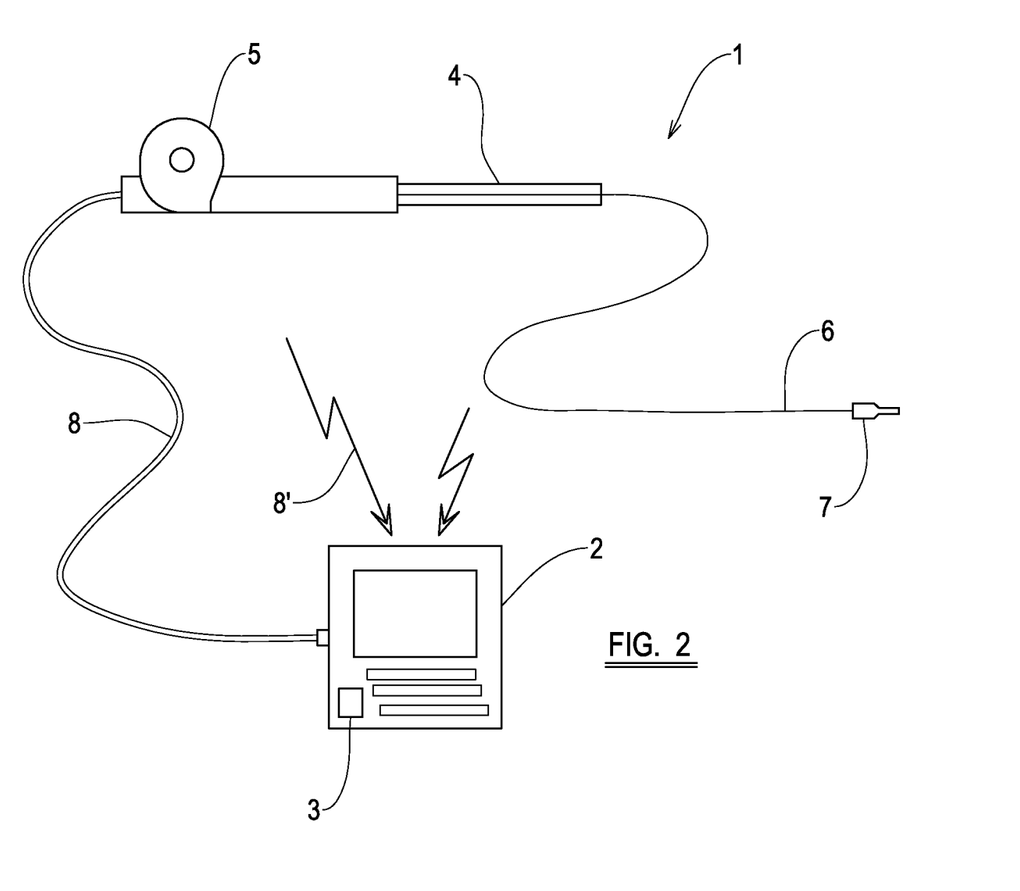
FIG. 2 is a schematic diagram of a system embodying the present invention.

Referring to FIG. 2, a system 1 embodying the invention for characterising a narrowing in a fluid filled tube comprises haemodynamic equipment 2 including a processor 3, a catheter 4, a motor drive 5 and an intra-arterial probe 6 such as an intra-arterial pressure wire (WaveWire or Combowire (Volcano Corp.) or Radi pressure wire (St Jude Medical) with a pressure measurement transducer or sensor 7—i.e. a device measuring pressure (P). Preferably, the probe 6 comprises the wire and the sensor 7 integrated in the wire. The sensor 7 is shown in situ in FIG. 3.

The processor 3 analyses and operates on the measurements taken by the sensor 7. A signal line 8 relays the pressure measurement signal from the sensor 7 to the processor 3. The signal line 8 is illustrated both as a wired connection 8 and as a wireless connection 8' from either the motor drive 5, the catheter 4 or direct from the transducer 7—any configuration is available.

The processor 3 operates on the measurements received from the transducer 7 in accordance with a number of algorithms which are discussed in greater detail below.

The sensor 7 is a pressure measurement sensor but other forms of sensor are envisaged; flow sensors, for example. Additionally, a capacitive sensor for measuring or calculating a thickness of an arterial wall is within the scope of the invention.

The system 1 may be provided in the following configurations or combination of configurations, but these are not an exhaustive list of configurations:
i. a stand-alone device incorporating a probe with pressure measurement capacity in wired connection with a processor to provide on-device analysis;
ii. a device incorporating a probe with pressure measurement capacity in wireless connection with a processor to provide analysis at the processor;
iii. a stand-alone device incorporating a probe with pressure measurement capacity and a data storage device operable to record measurement data for real time or subsequent communication to a processor to provide analysis at the processor (real time and/or off-line); and
iv. a device incorporating a probe with pressure measurement capacity in wireless connection with a data storage device operable to record measurement data for real time or subsequent communication to a processor to provide analysis at the processor (real time and/or off-line).

In the cardiac environment where the system 1 is configured as part of haemodynamic equipment, the system is configured using the processor 3 in the haemodynamic equipment, such as in McKesson equipment—Horizon Cardiology™, a cardiovascular information system (CVIS). The processor can be configured as supplemental to the haemodynamic equipment. Such configurations are particularly effective for the equipment processor to perform off-line analysis of the pressure data.

The system 1 can be used in combination with other haemodynamic equipment, medical imaging equipment and/or in-patient marker location equipment.

The system is used for profiling or characterising a narrowing in a fluid filled tube. An example of the use of such a system is in the cardiac environment when the tube is an artery and the narrowing/restriction/constriction in the tube is a stenosis.

The basic system components are: the probe 6 having a measurement sensor 7 to take an instantaneous measurement at different locations along the tube; the motor drive 5 to draw the probe 6 at a predetermined rate through the tube; and the processor 3 to calculate, from the instantaneous measurements, a characteristic of the tube at different locations along the tube. In this example a particularly useful measurement to sense is that of pressure as a pressure drop results following the fluid passing through a restriction.

A profile or assessment of a restriction to flow is made by expressing the ratio of distal to proximal pressures within the tube. This measures the total restriction to flow across all stenoses along the length of the tube from position D1 to D3 where the respective pressure measurements are taken and expressed as a ratio (P4/Pi) either with or without conditions of maximal hyperemia.

In addition to calculation of the total restriction to flow along a vessel, it is possible to calculate the instantaneous pressure drop across an individual stenosis from the ratios of pressure in segments D distance apart. For example the ratio of fall in pressure over distance $D_3$ is:

$$\text{Instantaneous Pressure ratio}(R_2) = \frac{P_4}{P_2}$$

which is approximately identical to the normalised instantaneous pressure ratio (nIPR):

$$\text{Normalised Instantaneous Pressure Ratio}(R_2) = \frac{\frac{P_4}{P_1}}{\frac{P_2}{P_1}}$$

Figure 3:
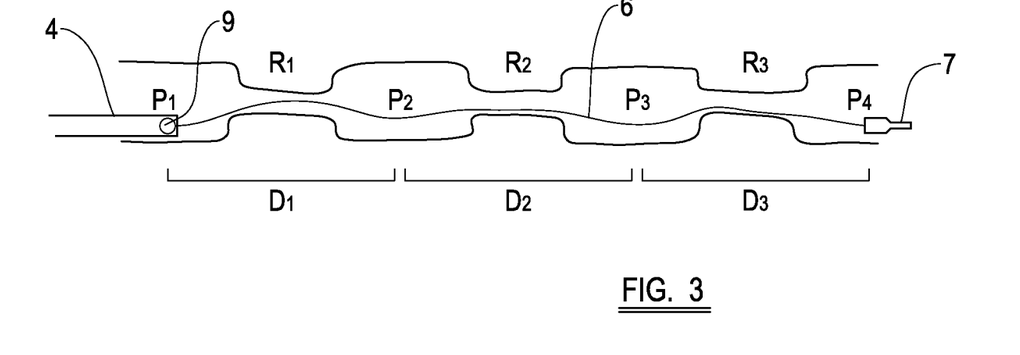
FIG. 3 is a schematic diagram of part of the system of FIG. 2 located in a fluid filled tube.

In one example, there are two measurement sensors displaced from one another—see FIG. 3. This system 1 has a further sensor 9 so that two instantaneous measurements are taken, one by the further sensor 9 at a substantially constant location along the tube and another by the first sensor 7 at different locations along the tube. The line or wire between the two sensors is drawable through the tube to alter the distance between the first sensor and the second sensor. One sensor (9 in this example) is fixed at the substantially constant location. The other sensor (7 in this example) moves relative to the one sensor 9. The "fixed" sensor 9 is located at the end of the catheter 4 from which the wire 6 carrying the other sensor 7 emanates. The probe sensor 7 therefore moves relative to the fixed sensor 9. The measurements are normalised with respect to the measurements taken at the substantially constant or fixed location.

The normalised instantaneous pressure ratio is more robust, as each distal value is normalised to the proximal aortic pressure, thus making comparisons along the length of the vessel more reliable as perturbations in absolute pressure are minimised.

Figure 5:
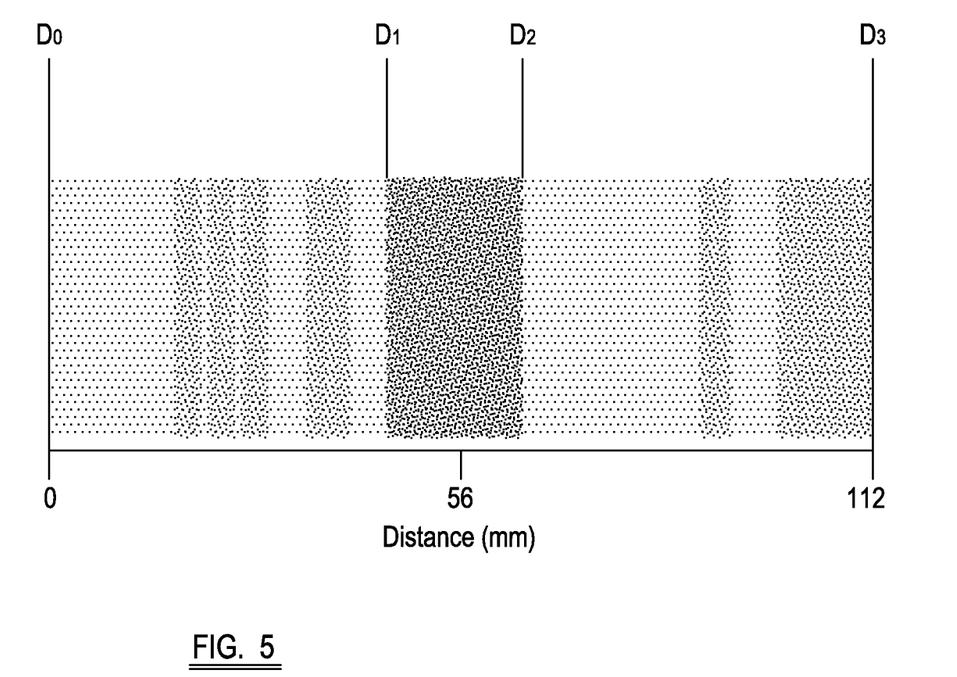
FIG. 5 is a point-by-point constriction intensity map generated following one embodiment of the present invention and based on the FIG. 4 data, in this example, the point-by-point assessment is of a stenosis in an artery, where $D_0$ is the start of a recording, $D_1$ is a point at the start of high stenosis intensity, $D_2$ is a point at the end of high stenosis intensity and $D_3$ is the end of the recording.

Systematically moving back along the vessel, at velocity U, and logging the instantaneous measurements alongside the draw distance for the probe create a pressure ratio (Ri, $R_2$, and R3 etc.) for each position (D1, D2, and D3 etc.) as shown in FIG. 5. The profiling or assessment of stenosis can be performed using either the normalised instantaneous pressure ratio or the instantaneous pressure ratio.

In one example, the predetermined rate of draw through the tube of the probe is a known and preferably constant speed. The draw is a known velocity draw to allow instantaneous pressure measurements to be taken as the probe is being drawn along the tube, for those measurements to be recorded as pressure measurements and for a pressure ratio to be calculated for each position of the probe along the tube.

The motor drive 5 is controlled, preferably by the processor 3, to draw the probe 6 back toward the catheter 4. The control may involve use of a feedback loop.

The systematic assessment of pressure along a vessel is performed by withdrawing the pressure sensor, at velocity U. Pressure is recorded at each location. It is possible to minimise error and to speed up the acquisition phase by using a feedback loop. In this feedback loop, the sensor is positioned in the tube, and then attached to the variable speed motor drive, or stepper motor. After sampling for a period of x seconds to establish a baseline for the measurements being taken and characteristics calculated, in this case NIPR or IPR mean and standard deviation moving averages, the motor drive commences pullback of the probe at velocity U. Sampling can also be over a fraction or specific time point of a beat.

Using high sampling frequencies and an appropriate sensor with a suitable frequency response, the pullback velocity U can be made faster by looking at a partial cardiac cycle in a single beat over a known distance.

Figure 6:
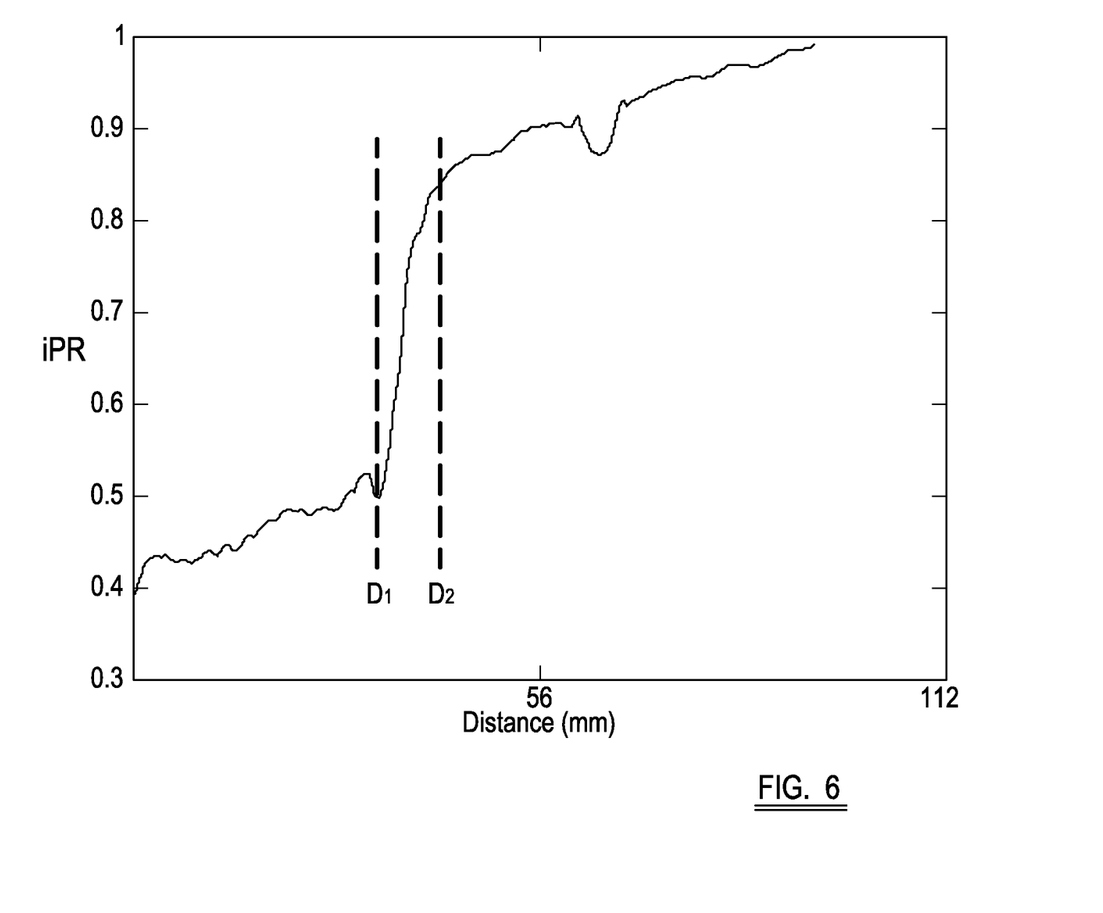
FIG. 6 is a plot created using a method embodying the present invention illustrating the IPR for a length of artery and a likely site for a stent along the tube between locations D1 and D2.

Pressure measurements are fed to the processor in the control console, and IFR or nIFR is calculated. This live pressure is compared against the moving average mean and standard deviation for the proceeding n beats, in a cardiac environment. If the live pressure data falls within the tolerance threshold, the motor continue with the pullback. If however the live pressure data falls outside of the tolerance threshold, the motor is paused and further measurements of pressure are made. Once pressure measurement falls within the tolerance threshold the motor continues with the pullback. A serial assessment or profile is created by this method. The feedback loop example is illustrated in FIG. 6.

In another example, the draw is stepped through the tube with at least one instantaneous measurement being taken at each location along the tube. The probe is then drawn through the tube for a predetermined distance, stopped and then another at least one instantaneous measurement is taken at the next location and so on. Preferably but not necessarily, the predetermined distance is a constant distance.

Each instantaneous measurement is logged as being at a respective location or with respect to a draw distance.

An alternative system embodying the invention has a position sensor fitted which monitors the position of the pressure sensor wire whilst being pulled back through the tube. In this way, each distance point/position/location would be linked or cross-referenced to a specific pressure measurement. Specifically, the position sensor monitors the guide wire holding the pressure sensor.

Figure 9:
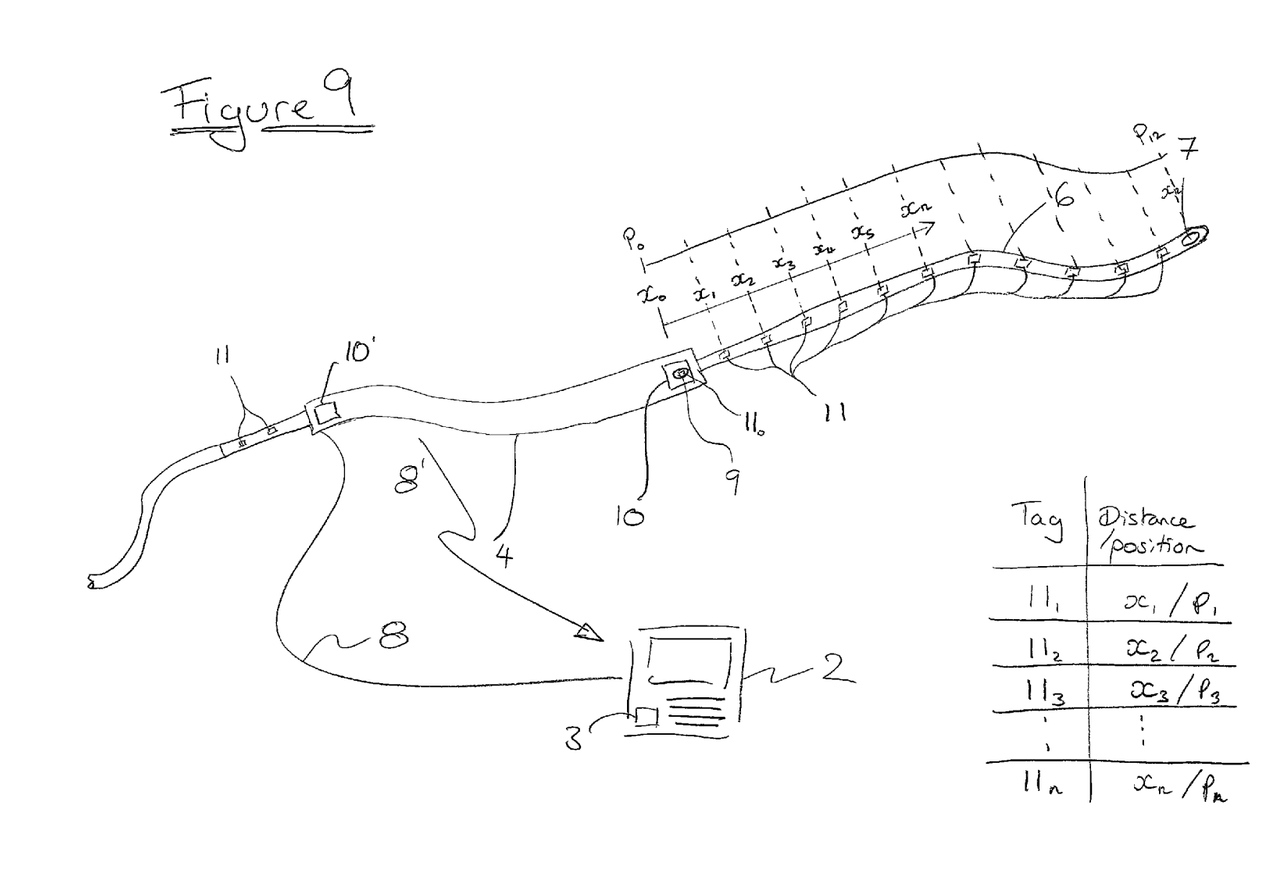
FIG. 9 is a schematic diagram of another system embodying the present invention.

Referring now to FIG. 9 another embodiment of the system is described which may operate with or without a motor drive 5. In the embodiments shown in FIG. 2, the system relies upon the motor to operate in a known way to determine the distance x along the line 6 to the sensor 7. Other mechanisms for determining the distance x to the sensor from a known point, usually on the catheter, may be used to take measurements at different known positions of x. In a purely manual version of the system, the line 6 may be drawn back through the catheter 4 manually and markings on the line 6 in the form of physical indicia can convey the distance x to the user. The system takes the position measure by reading the markings or marker on the probe. The marker may be a visible indicator read by a laser position indicator.

A semi-automatic version of the system can use a manually drawn line 6 through the catheter 4 and a combination of i) an RF reader 10 positioned preferably at the head of the catheter 4 from which the line 6 projects a distance x out of the catheter 4 and ii) multiple RF tags 1 1 positioned along the line 6. The line 6 is provided with a series of equispaced passive RF tags 1 1 each having an individual identifier which is read when in close (if not only immediate) proximity to the reader 10. In one embodiment, the RF tag reader 10 is in a coincident position with the second sensor 9 mounted at the head of the catheter 4. Coincidence of these two elements is not essential. More than one RF tag reader 10 can be used on the catheter.

A lookup table stored locally or in the processor 3 takes the read information from the reader 10 and identifies the tag adjacent the reader 10 for example as tag 1 1 o and identifies from the lookup table that tag 1 1₀ which is positioned at the reader 10 is a distance x away from the sensor 7 along the line 6 meaning that the sensor 7 is at known position $Pi_2$ The line is then drawn through until another RF tag 1 1 is read by the reader 10 at which point that tag is identified, its position is known as being at the reader 10 and the distance from that tag to the sensor 7 is also known so the position of the sensor 7 is known. This process is repeated and tags 1 1 are identified, the sensor 7 position is identified as known and at least one measurement is taken at the known position.

Preferably, the RF tags 11 are equispaced along the line 6 but they need not be equispaced as their positions along the line 6 relative to the sensor 7 is the only essential data to be associated with each tag. This essential data need not be present at the time the measurements are taken. Measurements can be taken and logged against each RF tag identifier and then subsequently the line can be measured to provide the relative position information for each tag and then that position information is associated with the measurement taken at each tag.

Preferably, the RF tags 11 are passive RF tags. The RF tags 11 could be active RF tags powered by a conductor in the line 6.

Figure 4:
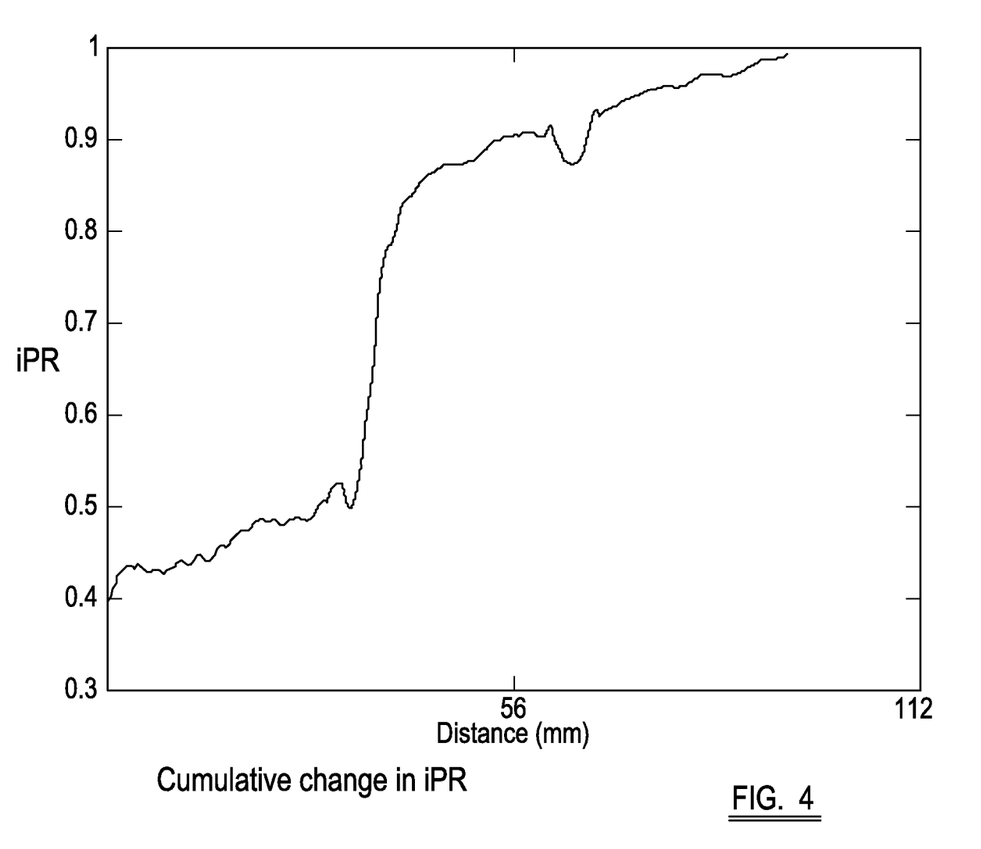
FIG. 4 is a plot created using a method embodying the present invention illustrating the IPR for a length of artery.

Examples of the invention allow a serial assessment of pressure ratio along a vessel. A rate of change of pressure or a rate of change of pressure ratio is further calculated to provide a measure of stenosis intensity. The rate of change in pressure or stenosis intensity at any position is calculated as which can be plotted as a point-by-point stenosis intensity map as shown in FIG. 4.

$$\text{stenosis intensity} = \frac{dIPR}{dt}$$

A systematic assessment is made at rate L/over time t, (known velocity example) so it is possible to calculate the withdrawal distance and thus the physiological stenosis length. In this example, this is the length (D2-D7) a segment which has the greatest physiological impact. The characteristic of the tube or further characteristics derived from the characteristic of the tube can be assessed and thresholded. This process can be automated using a search algorithm which looks for points at which the IPR or nIPR exceeds a given threshold (in this example D1 and D2).

physiological stenosis length=$D_1$-$D_1$

The characteristics and/or derived characteristics are used to assess or profile the tube to identify the length and/or location of a narrowing of the tube along the tube length. The use of thresholding techniques for the various characteristics and/or derived characteristics identifies regions of the tube where the thresholds are exceeded allowing identification and locating of stenosis and their length.

An example of a derived characteristic of the tube is the cumulative burden on the tube caused by a narrowing in the tube. It is possible to calculate the individual stenosis burden or stenosis occlusive value (with time points D? start of a stenosis, and $D_2$ end of a stenosis):

instantaneous stenosis burden=$\int D_1^D 1IPR$

Or, normalised instantaneous stenosis burden=$\int_{D_2}^D 2nIPR$ and total stenosis burden (over time points $D_0$ to $D_3$) for the entire vessel, total stenosis burden=$\int_{D_2}^{D}2\text{IPR}$ Or normalised total stenosis burden=$\int_{D_1}^{D}1\text{nIPR}$ Virtual angioplasty assessment is enabled by examples of the present invention.

Figure 7:
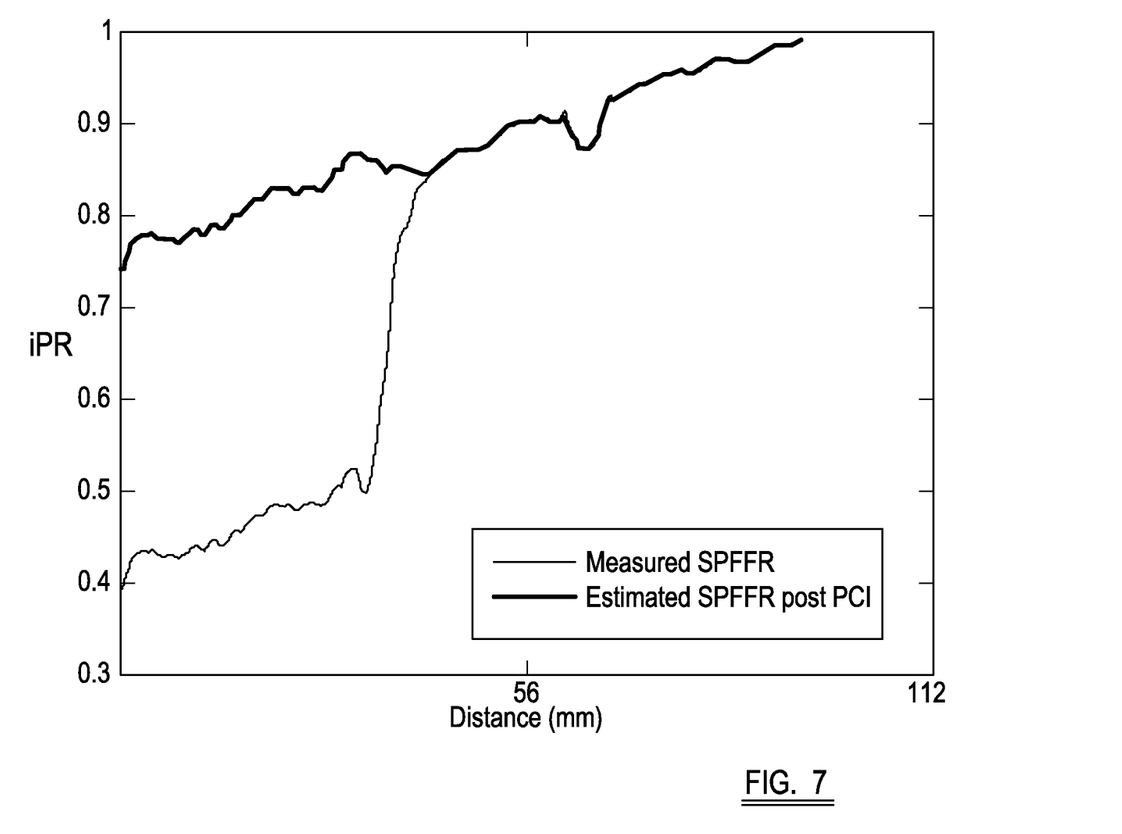
FIG. 7 is a plot illustrating the likely effect on the same characteristic, IPR, on the artery after a hypothetical angioplasty procedure of locating a stent along the tube between locations D1 and D2 together with a plot of the measured values of IPR obtained using a method embodying the present invention.
Figure 8:
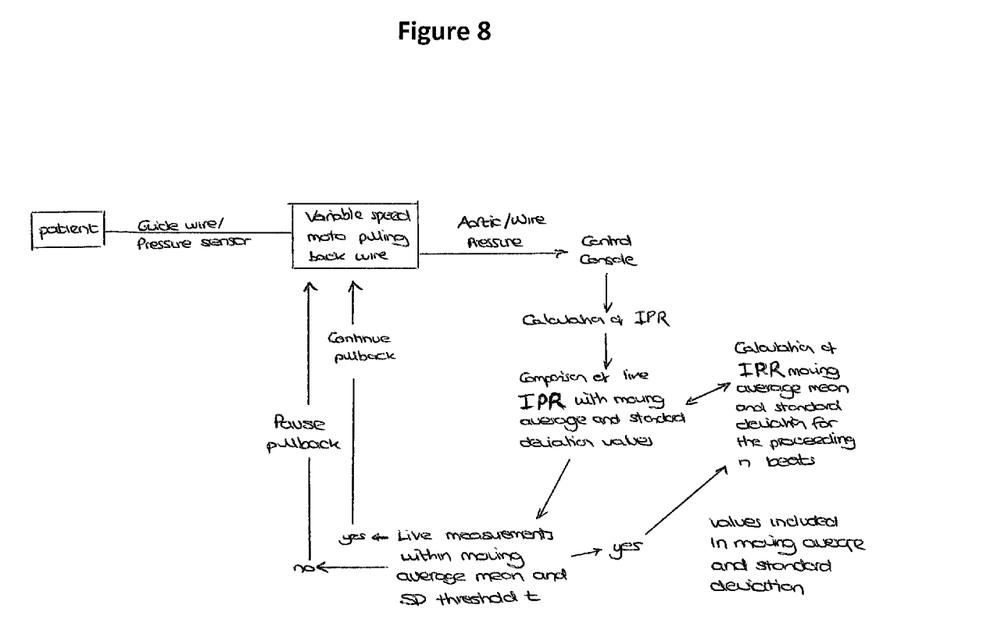
FIG. 8 is a flowchart showing operation of a system embodying the present invention incorporating a feedback procedure.

Referring to FIG. 6, a systematic assessment approach is applied and the measured profile is displayed. The segment of tube to which a stent or other angioplasty is to be applied (having a high stenosis grade ($D_i$–$D_2$)) has its profile characteristic estimated with the stent applied and then subtracted away on an individual segment basis to give a compensated profile as shown in FIG. 7. It is therefore possible to assess the effects of angioplasty on IPR of nIPR prior to treatment.

Virtual$IPR_{D_0\_D_1}$=$IPR_{D_0\_D_2}$+$\Delta IPR_{D_2\_D_1}$ or

Virtual $nIPR_{D_0\_D_1}$=$niPR_{D_0\_D_1}$+$\Delta niPR_{d_0\_D_2}$

Where $D_0$ is distance=0, $D_1$ the distance at the start of the high stenosis grade, and $D_2$ the distance at the end of the high stenosis grade.

Such virtual assessment or profiling of a tube or stenosis in a tube using either IPR or nIPR allows the effects of removing a stenosis to be assessed prior to performing the procedure itself.

There are particular needs in the cardiac environment for simplified equipment having the smallest possible footprint (or being the least invasive requiring the smallest possible entry site) so the provision of a known position probe to assess or profile stenoses along the length of the tube represents a significant technical advance in that field.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A system for characterizing a narrowing in a fluid filled blood vessel, the system comprising:
a pressure-sensing guidewire comprising a first pressure sensor to take instantaneous pressure measurements at different locations along the blood vessel without conditions of maximal hyperemia;
a mechanism to draw the pressure-sensing guidewire through the blood vessel; and
a processor in communication with the pressure-sensing guidewire and configured to:
compare an instantaneous pressure measurement to a range based on a moving average for a preceding number of cardiac cycles and cause the mechanism to at least one of:
draw the pressure-sensing guidewire through the blood vessel if the instantaneous pressure measurement is within the range; or
pause movement of the pressure-sensing guidewire if the instantaneous pressure measurement is outside the range;
calculate a pressure ratio at the different locations along the blood vessel using the instantaneous pressure measurements obtained by the first pressure sensor without conditions of maximal hyperemia at each of the different locations and instantaneous pressure measurements obtained by a second pressure sensor without conditions of maximal hyperemia at a substantially fixed location in the blood vessel, wherein the instantaneous pressure measurements are obtained at each of the different locations over a partial cardiac cycle of a single heart beat; and
output to a display a visual representation of the calculated pressure ratios at the different locations along the blood vessel.

2. The system of claim 1, wherein the mechanism is a motorized mechanism.

3. The system of claim 1, wherein the mechanism is a manual mechanism.

4. The system of claim 1, further comprising a position measuring device to provide location data relating to a location at which a respective instantaneous pressure measurement is taken by the first pressure sensor, wherein the position measuring device is a reader to read a marker on the pressure-sensing guidewire.

5. The system of claim 4, wherein the marker on the pressure-sensing guidewire is an RF tag.

6. The system of claim 4, wherein the reader is an RF reader.

7. The system of claim 1, further comprising a position measuring device to provide location data relating to a location at which a respective instantaneous pressure measurement is taken by the first pressure sensor, wherein the position measuring device provides a relative location of the first pressure sensor with respect to a known datum.

8. The system of claim 1, further comprising a position measuring device to provide location data relating to a location at which a respective instantaneous pressure measurement is taken by the first pressure sensor, wherein the position measuring device provides an absolute location of the first pressure sensor.

9. The system of claim 1, wherein the range is further based on a standard deviation.

10. The system of claim 1, further comprising the second pressure sensor to take the instantaneous measurements at the substantially fixed location in the blood vessel as the first pressure sensor takes the instantaneous measurements at the different locations along the blood vessel.

11. The system of claim 10, wherein the calculated pressure ratio is normalized with respect to the substantially fixed location.

12. The system of claim 1, wherein the mechanism to draw the pressure-sensing guidewire through the blood vessel is configured to draw the pressure-sensing guidewire at a predetermined rate through the blood vessel.

13. The system of claim 12, wherein the predetermined rate is a constant speed.

14. The system of claim 12, wherein the predetermined rate is stepped draw having a predetermined distance for each step.

15. The system of claim 14, wherein the predetermined distance is a constant distance.

16. The system of claim 14, wherein the processor is further configured to: record the instantaneous pressure measurements and calculate the pressure ratio for each stepped position of the pressure-sensing guidewire along the blood vessel.

17. The system of claim 1, wherein each instantaneous measurement is logged at a respective location or with respect to a draw distance.

18. The system of claim 1, wherein the pressure ratio represents a restriction to flow along the blood vessel.

19. The system of claim 1, wherein the processor is further configured to calculate a measure of stenosis intensity.

20. The system of claim 19, wherein the measure of stenosis intensity is calculated as a rate of change in the instantaneous pressure measurements.

21. The system of claim 19, wherein the measure of stenosis intensity is calculated as a rate of change in the calculated pressure ratios.

22. The system of claim 19, wherein the processor is further configured to output to the display a visual representation of the calculated measure of stenosis intensity.

23. The system of claim 22, wherein the visual representation of the calculated measure of stenosis intensity is a point-by-point stenosis intensity map.

24. The system of claim 22, wherein the processor is further configured to modify the visual representation of the calculated pressure ratios along the blood vessel to simulate treatment.

25. The system of claim 24, wherein the treatment comprises application of at least one of a stent or an angioplasty procedure.

26. The system of claim 1, wherein, based on the calculated pressure ratio, the processor is configured to control the mechanism to at least one of draw the pressure-sensing guidewire through the blood vessel or pause movement of the pressure-sensing guidewire.

27. The system of claim 1, wherein the instantaneous pressure measurements are obtained by the first pressure sensor at a position distal of the narrowing in the fluid filled blood vessel, and wherein the instantaneous pressure measurements are obtained by the second pressure sensor at a position proximal of the narrowing in the fluid filled blood vessel.

28. The system of claim 1, wherein the first pressure sensor comprises a transducer.

29. The system of claim 1, wherein the first pressure sensor is disposed at a distal end of the pressure-sensing guidewire.

30. The system of claim 29, wherein the pressure-sensing guidewire and the pressure-sensing catheter are arranged such that the pressure-sensing guidewire moves within the pressure-sensing catheter while the mechanism draws the pressure-sensing guidewire through the blood vessel.

31. The system of claim 1, further comprising a pressure-sensing catheter comprising the second pressure sensor.

32. A system for characterizing a narrowing in a fluid filled blood vessel, the system comprising:
a pressure-sensing guidewire comprising a first pressure sensor to take instantaneous pressure measurements at different locations along the blood vessel without conditions of maximal hyperemia;
a mechanism to draw the pressure-sensing guidewire through the blood vessel; and
a processor in communication with the pressure-sensing guidewire and configured to:
calculate a pressure ratio at the different locations along the blood vessel using the instantaneous pressure measurements obtained by the first pressure sensor without conditions of maximal hyperemia at each of the different locations and instantaneous pressure measurements obtained by a second pressure sensor without conditions of maximal hyperemia at a substantially fixed location in the blood vessel, wherein the instantaneous pressure measurements are obtained at each of the different locations over a partial cardiac cycle of a single heart beat;
compare the calculated pressure ratio to a range based on a moving average for a preceding number of cardiac cycles and, based on the comparison, control the mechanism to at least one of draw the pressure-sensing guidewire through the blood vessel or pause movement of the pressure-sensing guidewire; and
output to a display a visual representation of the calculated pressure ratios at the different locations along the blood vessel.

33. The system of claim 32, wherein the range is further based on a standard deviation.

34. The system of claim 32, wherein, based on an instantaneous pressure measurement, the processor is configured to control the mechanism to at least one of draw the pressure-sensing guidewire through the blood vessel or pause movement of the pressure-sensing guidewire.

* * * * *